United States Patent [19]
Anderson

[11] Patent Number: 5,336,221
[45] Date of Patent: Aug. 9, 1994

[54] METHOD AND APPARATUS FOR APPLYING THERMAL ENERGY TO TISSUE USING A CLAMP

[75] Inventor: Dallas W. Anderson, The Woodlands, Tex.

[73] Assignee: Premier Laser Systems, Inc., Irvine, Calif.

[21] Appl. No.: 972,530

[22] Filed: Nov. 6, 1992

Related U.S. Application Data

[63] Continuation-in-part of Ser. No. 961,165, Oct. 14, 1992, abandoned.

[51] Int. Cl.$^5$ .................................... A61B 17/04
[52] U.S. Cl. .................................... 606/27; 606/205; 606/8; 606/150
[58] Field of Search ............... 606/27, 3, 2, 8, 9, 606/15, 16, 40, 51, 52, 49, 205, 208, 209, 150

[56] References Cited

U.S. PATENT DOCUMENTS

| | | | |
|---|---|---|---|
| 4,597,379 | 7/1986 | Kihn et al. | 606/205 |
| 4,633,870 | 1/1987 | Malyshev | 606/8 |
| 4,672,969 | 6/1987 | Dew | 606/8 X |
| 4,892,098 | 1/1990 | Sauer | 606/8 X |
| 4,985,030 | 1/1991 | Melzer et al. | 606/51 |
| 5,151,102 | 9/1992 | Kamiyama et al. | 606/51 |
| 5,156,613 | 10/1992 | Sawyer | 606/8 X |

*Primary Examiner*—Stephen C. Pellegrino
*Attorney, Agent, or Firm*—Steven C. Stewart; James H. Beusse

[57] ABSTRACT

A method and apparatus for applying optical or other thermal energy to tissue using a clamp. The energy is supplied at a frequency which biologically welds or fuses tissue. A material that is transmissive to the energy treatment frequency is embedded in one or more jaws of the clamp and engage the tissue during the tissue fusion process. The transmissive material has a thickness selected to insure that the energy source is spaced at the proper distance from the tissue so that the tissue receives the proper amount of energy for sealing. The transmissive material holds the tissue in the jaw to maintain the edges of the tissue in tight approximation. The energy may be coupled to the clamp by one or more optical fibers. These fibers are recessed in or placed adjacent to the jaw at a specified distance from the surface of the transmissive material and directs treatment energy through the transmissive material to weld the edges of the tissue together.

4 Claims, 3 Drawing Sheets

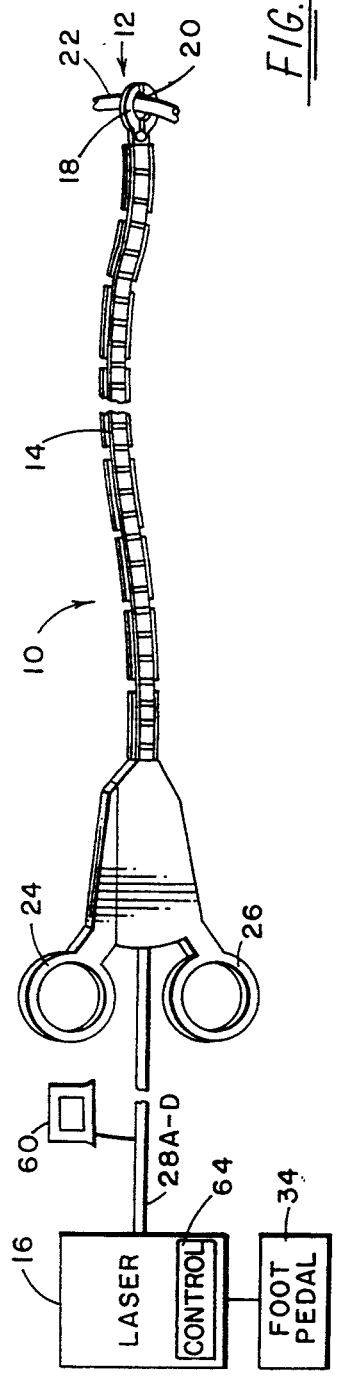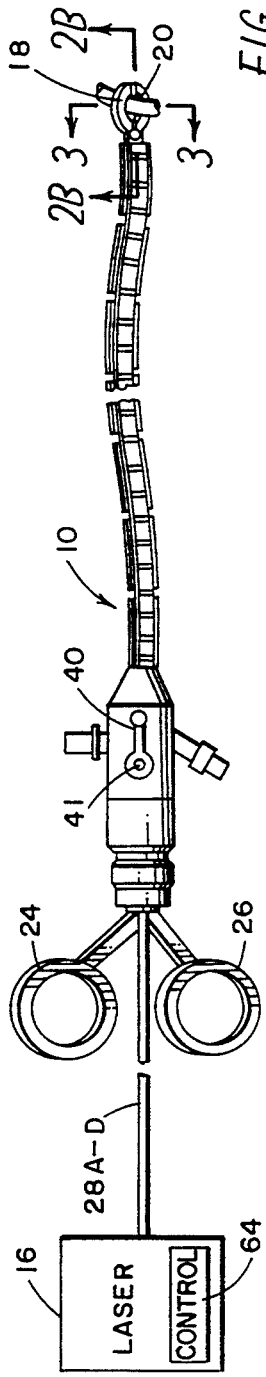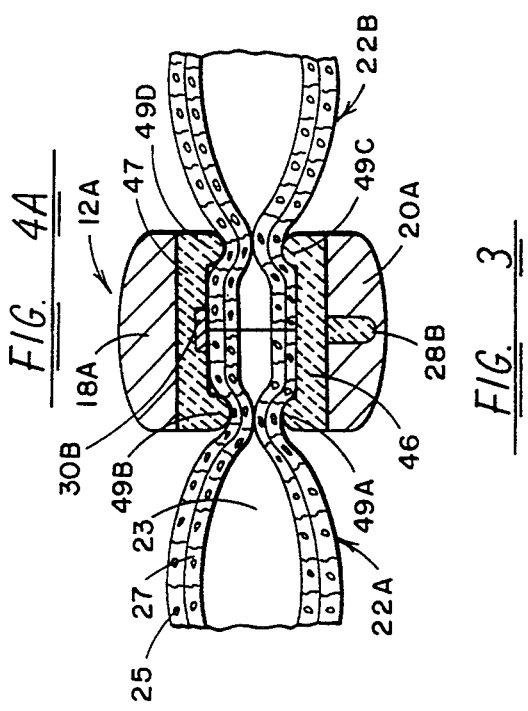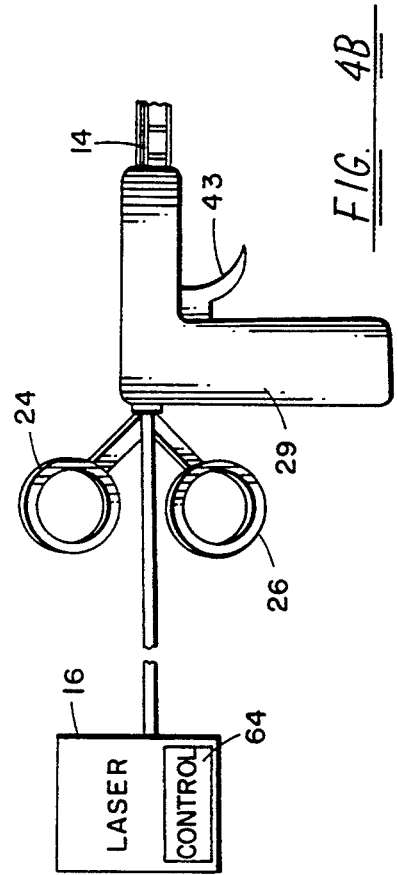

METHOD AND APPARATUS FOR APPLYING THERMAL ENERGY TO TISSUE USING A CLAMP

This is a Continuation-In-Part of application Ser. No. 07/961165, filed Oct. 14, 1992.

BACKGROUND OF THE INVENTION

This invention relates to a method and apparatus for applying thermal energy to biological tissue whereby tissue is converted to a denatured proteinaceous substance to join tightly approximated tissue segments, and, more particularly, to a method and apparatus for reconstructing severed tissue, including vessels and ducts by use of a clamp which is constructed to hold edges of the tissue in tight proximity while directing heat energy onto the tissue to denature the proteinaceous substance therein.

Optical energy has been used to convert biological tissue into a denatured collagenous substance for facilitating healing and wound closure. This healing technique is referred to generally as laser tissue welding. Examples of such laser tissue welding methods are described in U.S. Pat. Nos. 4,672,969, 4,854,320, 5,002,051, and 5,140,984. These methods deliver optical energy to tightly approximated tissue in the vicinity of a wound. This application of thermal energy results in the denaturation of tissue protein including collagen, with disruption of the cell walls which allow the intra- and intercellular fluids to mix. Additional heat further denatures this protein soup which binds together creating something akin to a "biological glue".

In many prior methods of optical energy wound closure, such energy is delivered through an optical fiber to the tissue being reconstructed. Typically one end of the fiber is connected to a laser that supplies optical energy to the wound site. Another end of the fiber is typically spaced a predetermined distance from the tissue, depending on the tissue type. A foot pedal or hand held device activates and deactivates the laser. The parameters such as intensity and duration of the optical energy are controlled so that substantially all of the tissue being heated is raised to a predetermined non-destructive temperature. The minimum predetermined temperature is one at which tissue is converted to a denatured collagenous substance. The maximum predetermined temperature is one at which water in the tissue boils.

Other methods known for healing and wound closure include suturing and stapling. These methods are often used in minimally invasive surgery in combination with various types of scopes, such as, for example, endoscopes, laparoscope, arthroscopes, etc. These scopes along with other medical equipment are inserted by a surgeon through incisions in the patient and then moved to the wound area being repaired. The scope is connected to a monitor so that the surgeon can view the procedure while the surgery is being performed.

Laser tissue welding may be used in minimally invasive surgery to repair vessels; however, conducting certain minimally invasive operations using current laser surgery techniques is long and tedious as the surgeon must weld at successive points along the circumference of the vessel or duct. This tissue welding process is further complicated as the distal end of the optic media that directs the laser doing the welding must be placed a predetermined distance to the tissue being reconstructed. If the distal end is not a predetermined distance from the area being reconstructed, the tissue would be temperature outside the aforementioned predetermined temperature sealing range. A drawback to prior welding methods is that it is difficult to place edges of tissue being repaired in close approximation. Placing the edges in tight proximity is necessary to insure proper denaturation and intercellular fusion of the tissue.

It is also desirable during surgery to occlude vessels. Occluding the vessel typically requires that clips or sutures be placed on the vessel to clamp the vessel shut. Clips, suture and staples left in the tissue are foreign bodies that can later have adverse effect on the patient.

SUMMARY OF THE INVENTION

An object of this invention is to provide an improved method and apparatus for reconstructing tissue, ducts, or vessels.

Another object of this invention is to provide an apparatus through which laser welding energy passes and is directed at tissue that is to be sealed, fused, or ligated.

It is also an object of this invention to cause the formation of a proteinaceous framework from denatured protein in the vicinity of biological tissue to seal tissue, ducts, and vessels.

It is an additional object of the invention to occlude or ligate off vessels and ducts by applying sufficient optical energy to the vessels so that the walls of the lumen are sealed tightly together and thereby occlude any lumen flow.

It is also an object of this invention to reconstruct vessels and ducts with a laser that is directed to areas completely circumscribing the vessel.

It is further an object of this invention to reconstruct tissue with any energy source, such as ultrasonic or any heat source, while maintaining at all times proper distance between a media delivering the energy to the tissue itself so that the final temperature of the tissue may be precisely maintained.

These and other objects are accomplished with an apparatus for causing the formation of the proteinaceous framework from denatured proteins and other tissue constituents, in the vicinity of biological tissue to be reconstructed. The apparatus includes a clamp with a concave surface and a layer of transmissive material that engages the tissue. An energy source is provided that supplies energy capable of heating the tissue to form an adhesive denatured proteinaceous substance, and the energy is delivered to the source through the transmissive material to the area on the biological tissue to be reconstructed when the tissue is engaged.

The energy directed at the area is controlled to be within a non-destructive range bounded by a minimum rate at which tissue forms a denatured proteinaceous substance and a maximum rate at which water in the tissue boils. The transmissive material ensures a predetermined distance between the device delivering the energy and the tissue itself. Thus the energy directed at the area on tissue will be precisely maintained within the non-destructive range.

Preferably a sensor is also placed within the clamp that detects the energy transmitted to the tissue being treated and provides a signal corresponding to the detected energy. This signal is fed back to control the rate at which the energy is directed at the area. Optionally an optical sensing device can be placed on the forward portion of the clamp for generating a video signal that can be viewed on a monitor. With the delivery device on the same clamp, the apparatus can be used in minimally invasive surgery.

In another aspect of the invention an apparatus for occluding a vessel having a lumen is provided. The apparatus includes a clamp with a concave curvature shaped to completely and tightly close the lumen when the clamp engages the vessel. An energy source provides energy capable of heating the tissue to form an adhesive denatured proteinaceous substance. A device which seals through the walls of the lumen is included. This device directs energy from the source through the vessel engaged with a clamp to heat the tightly approximated walls of the lumen to the non-destructive range. As a result of the walls being heated and the intercellular matrix formation, the vessel lumen is occluded.

In a further aspect of the invention, a method for anastomosing a tissue is described. The method comprises the steps of placing the edges of the tissue in close to tight proximity to each other. The closely approximated edges of the tissue are clamped with sufficient pressure to force the edges into tight contact with each other. Energy is provided which is capable of heating the tissue to form a proteinaceous substance. This energy is directed from the source to the approximated tissue edges to heat the contacting edges of the tissue to the non-destructive range and thereby welds the tissue edges together. The energy from the source may be directed at multiple areas on the tissue either sequentially or simultaneously through an optic media.

BRIEF DESCRIPTION OF THE DRAWING

FIG. 1 is a perspective view of the invention having a clamp connected to one end of an optical energy source;

FIG. 2B is a clamp shown in FIG. 4A along line 2B—2B having a top and bottom jaw each with a transmissive surface that contacts tissue to be welded with a curvature for sealing the tissue by completely closing the lumen, and FIG. 2C is an alternate embodiment of the clamp shown in FIG. 2B with transmissive surface only on one jaw;

FIG. 3 is a front cross-section view along line 3—3 of FIG. 1;

FIG. 4A is a perspective view of an alternate embodiment invention shown in FIG. 1 having a trigger-type grip;

FIG. 4B is a perspective view of an alternate embodiment of the invention shown in FIG. 4A having another trigger-type grip;

DESCRIPTION OF THE PREFERRED EMBODIMENTS

Figure 2A:
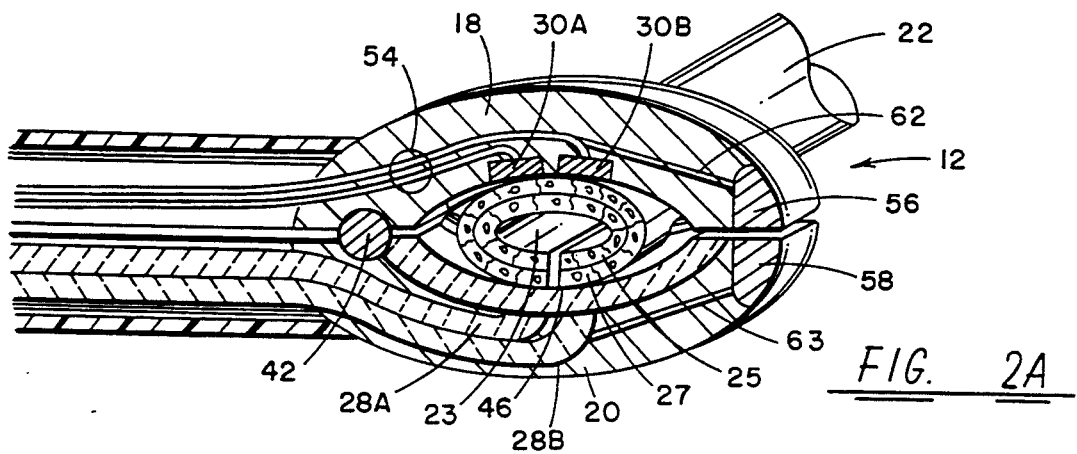
FIGS. 2A, 2B, and 2C are side cross-sectional views of the clamp, where 2A is a clamp shown in FIG. 1 having a curvature for approximating tissue.

Referring to FIG. 1, there is shown an apparatus 10 for tissue welding using a clamp 12 that is fed optical energy through conduit 14 from energy source 16. Preferably energy source 16 generates coherent light energy capable of heating tissue to form an adhesive denatured proteinaceous substance. Clamp 12 includes a first jaw 18 and a second jaw 20 which engage and disengage with tissue such as a duct or a vessel 22 in response to hand grips 24 and 26 being depressed and released by the user. Energy from the energy source 16 is fed through conduit 14 using optic media 28a–28b and 28c–28d (FIG. 2B) such as a fiber optic cable having proximate and distal ends. The proximate end of optic media 28a–d is optically connected to energy source 16. The distal end of fiber optic media 28a–28d terminates in clamp 12 and directs optical energy at the vessel 22.

Referring to FIGS. 2A, 2B, 3, and 5A–5C, vessel 22 typically has a lumen 23 through which fluid flows, surrounded by an outer layer 25 and an inner layer 27 of tissue. The use of the word vessels throughout is meant to include all tubular organs, such as ducts and arteries. The use of the word lumen is defined as a cavity or the channel within any organ or structure of the body. Clamp 12 engages with the inner layer 27 to seal lesions in the tissue (FIG. 2A), seal closely approximated edges of a transected vessel (FIGS. 2B, 3, 5A–5C), or occlude or close off the lumen within the vessel 22 (FIG. 2C).

Figure 2C:
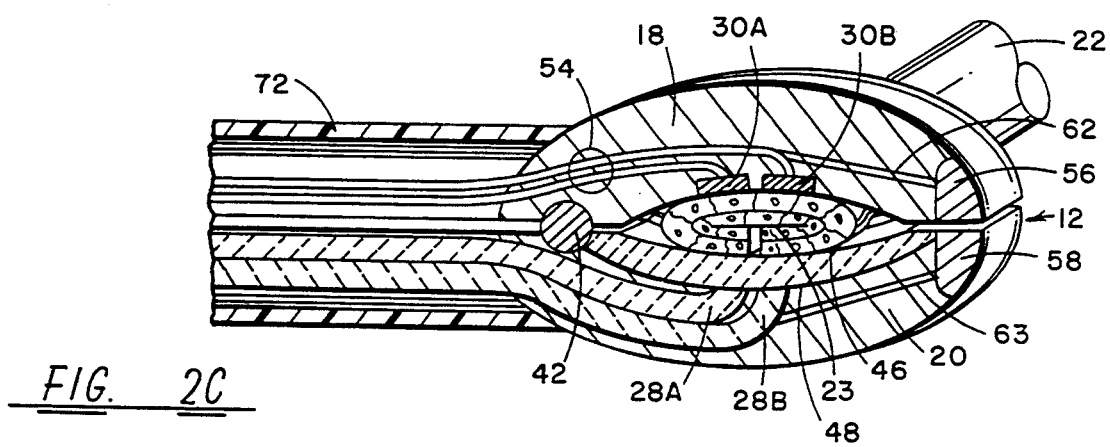
Figure 2B:
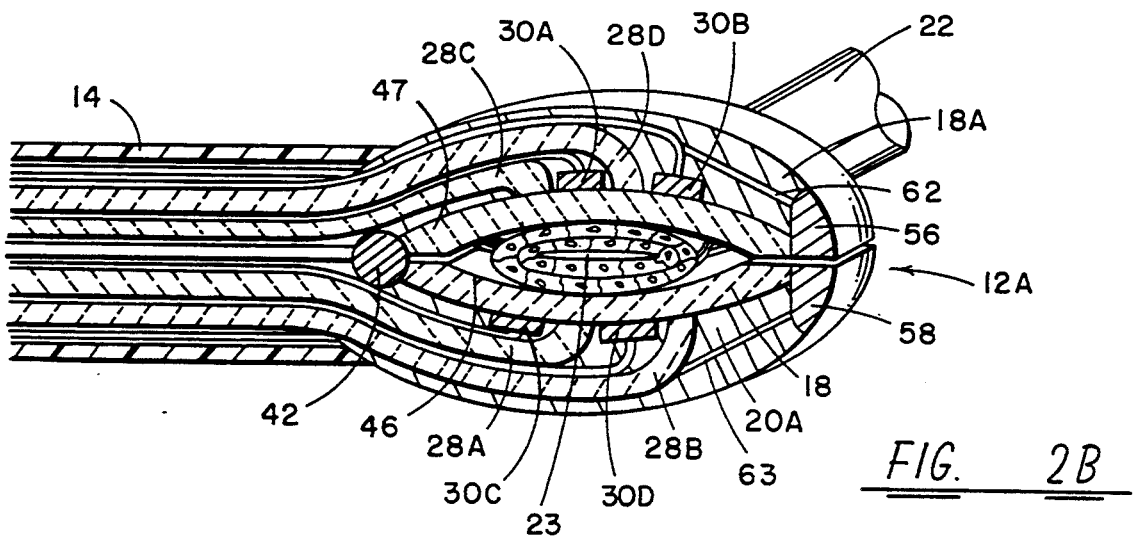

Referring to FIGS. 2A–2C, clamp 12 includes a plurality of feedback sensors 30a–30b and 30c–30d (FIG. 2B) which detect energy exiting fiber optic media 28a–28d either passing through the vessel 22, or changing the temperature of vessel 22. Feedback sensors 30a–30d convert detected energy to signals which are fed through line 54 to the energy source 16. Energy source 16 then responds to the detected energy signals by adjusting the energy fed to media 28a–28d to maintain the temperature of the tissue being heated within a predetermined range.

Energy source 16 is activated in response to a foot or hand pedal 34 being engaged and disengaged. The parameters in which energy source 16 feeds optical energy through fiber optic media 28a–28d is dependent on the thickness and type of tissue, organ, or vessel 22 to be reconstructed. Examples of these parameters and preferable distances between the ends of fiber optic media 28a–28d and the surface of tissue, organ, or vessel 22 are summarized in the following Table I. These parameters are by no means all exclusive; it is envisioned that other parameters can be used with modifications and it is intended that this table be exemplary of a preferred embodiment only.

TABLE I

| | LASER PARAMETERS FOR VARIOUS ORGAN TYPES | | | | | |
|---|---|---|---|---|---|---|
| Organ Type | Organ Thickness (mm) | Transparent Material Thickness (mm) | Spot Size Diameter (with 400μ fiber) (mm) | Range Of Power (Watts) | Exposure Duration On/Off | Approximate Final Energy Transferred to Organ (J/CM²) |
| Artery | 1 | 1 | .575–.646 | .5–.7 | 0.5 sec/0.5 sec | 4.63 |
| Fallopian Tube | 3 | 1 | .575–.646 | .65–.85 | 0.5 sec/0.5 sec | 5.79 |
| Tendon | 5 | 3 | .925–1.14 | .65–.85 | 1.0 sec/1.0 sec | 5.7 |

Referring to FIG. 4A, an alternate embodiment of apparatus 10 is shown having a hand trigger 40 pivotally connected with pin 41 to apparatus 10. This trigger 40 replaces foot pedal 34 and pivots about pin 41 to enable energy source 16. Referring to FIG. 4B, there is shown apparatus 29, an alternate embodiment of apparatus 10 shown in FIG. 1. Apparatus 29 has a trigger 43 that activates energy source 16 when depressed.

Referring to FIGS. 2A–2C, jaws 18 and 20 are shown pivotally connected to pin 42. A cable or other mechanism (not shown) force jaws 18 and 20 to rotate about pin 42 to engage and disengage vessel 22. Mechanisms for forcing jaws 18 and 20 to rotate about pin 42 are generally known.

Referring to FIG. 2B, there is shown clamp 12a, an alternate embodiment of apparatus 10 (FIG. 2A). Clamp 12a has sensors 30c–30d positioned on jaw 20a, and fiber optic media 28c–28d positioned on jaw 18a. Energy exits fiber optic media 28a–28d, and is directed through transmissive material surfaces 46 and 47 at one or more areas or spots that circumscribes vessel 22. Sensors 30a–30d either detect the energy emitting through vessel 22, or the amount of heat that is absorbed by vessel 22. Sensors 30a–30d may comprise conventional heat sensors whose impedance varies with temperature so as to provide an indication of the energy being delivered to vessel 22 and to enable a control 64 of energy source 16 in response to such temperature by being coupled to source 16 via leads 54.

The amount of heat absorbed by the vessel may be accomplished by first determining the amount of energy emitted by the source and then subtracting the amount of energy loss through the media to determined a delivered energy. The delivered energy is subtracted from the actual energy detected by the sensor to determine a delta which corresponds to the energy absorbed by the tissue. The energy source can then be controlled as a function of this delta.

Referring to FIGS. 3, 5A–5C, jaws 20a and 18a have respective surfaces 46 and 47 constructed with a layer of transmissive material shaped of generally concave curvature that engages with vessel 22. By transmission material it is intended to mean any material which is substantially transparent to the energy being emitted at the distal ends of media 28a–28d. Protrusions 49a–49d extend along the edges and inside surface 46 and 47 of the transmissive material and jaws 18a and 20a when jaws 18 and 20 are engaged, protrusions 49a–49d occludes lumen 23 to prevent fluid from passing through vessel 22. Also, while clamped, protrusions 49a–49d maintain the edges of vessel 22a in tight proximity to the edges of vessel 22b during the tissue fusion operation. In other words, protrusions 49a–49d create a side opening in clamp 12a which is smaller than the opening in the clamps center to prevent vessels 22a from separating from vessel 22b, and maintain tissue approximation.

Referring to FIGS. 2A–2C, the distal end of fiber optic media 28a–28d preferably terminates adjacent transmissive material surfaces 46 or 47. The thickness of the transmissive material is selected to maintain a predetermined distance between the end of fiber optic media 28a–28d and the surface of vessel being treated 22. The predetermined distance is selected in accordance with vessel 22 type and thickness. Sensors 30a–30b are placed across from the ends of fiber optic media 28a–28b to detect the optical energy being passed through tissue or vessel 22, or the optical energy being absorbed by the vessel 22.

Referring to FIGS. 1 and 4, energy source 16 contains a control 64 that adjusts the rate at which energy is delivered to the tissue to be within a nondestructive range bounded by a minimum rate at which tissue forms a denatured proteinaceous substance and a maximum rate at which water in the tissue would boil. An exemplary control device is described in U.S. Pat. No. 4,854,320 which is hereby incorporated by reference. Preferably the maximum rate is selected which is slightly below the rate at which shrinkage of this tissue type occurs so that shrinkage is prevented. Parameters of the rates at which the tissue is heated are previously described herein.

Referring to FIG. 2A–2C, photo sensors 56 and 58 are preferably placed or embedded in the forward most portion of jaws 18 and 20 respectively. Photo sensor 56 and 58 view the area forward of clamp 12 and generate video signals which are fed to a monitor 60 over a lines 62 and 63. Monitor 60 responds to this video signal by providing an image of the photo sensor's 56 and 58 view to the user. This view assists the user in placing the clamp 12 in the proper position to engage the duct, tissue, or vessel 22.

Referring to FIG. 2B and FIG. 3, the curvature of the transmissive material surfaces 46 and 47 are selected to engage vessel 22. Clamp 12a is preferably used to seal transected vessels 22a and 22b. First, the edges of the transected vessels 22a and 22b are placed in close or tight proximity. Next, jaws 18 and 20 engage the surface of the inner layer of the tissue 22a and 22b, while protrusions 49a and 49b engage vessel 22a, and protrusions 49c and 49d engage vessel 22b. This engagement forces an edge 65 of vessel 22a to contact edge 66 of vessel 22b to form a seam. Energy source 16 is then activated and energy is delivered through media 28a–28d to seam of vessel 22 to form a proteinaceous substance that seals the seam. The amount of energy provided and the duration of the energy being delivered is dependent on the tissue type and thickness as previously discussed.

It may be preferable prior to jaws 18a and 20a engaging vessel 22 that an expandable device (not shown) be inserted into the lumen 23. Edges 65 and 66 are then positioned in close proximity so that the seam of edges 65 and 66 surround the expandable device. The device is then expanded by any of several conventional means to assist in maintaining the integrity of the vessel when providing optical energy to the seam. The device is contracted and removed after the seam is sealed.

Optical energy may be delivered to the tissue simultaneously through media 28a–28d. Alternately, the optical energy may be delivered through each of media 28a–28d in a sequential manner, i.e. first through media 28a, then 28b and so on. The distal ends of media 28a–28d are placed in clamp 12 to deliver optical energy to a plurality of areas that completely circumscribe vessel 22 adjacent the transection.

Referring to FIG. 2C, there is shown a clamp 12a having jaw 18a and 20a that pivot about pin 42 in response to a mechanism (not shown) being activated by grips 24. Jaws 18a and 20a have tissue engaging concave surfaces that are curved to place additional pressure on the vessel, compressing the lumen 23 walls together of vessel 22. Once compressed by jaws 18a and 20a, energy is delivered through media 28a–28b, through transmissive material surface 46 and through vessel 22. When the energy is applied to the vessel for the proper duration and level as described above, the walls of the compressed lumen 23 are denatured, form a glue and bind together.

Figure 5A:
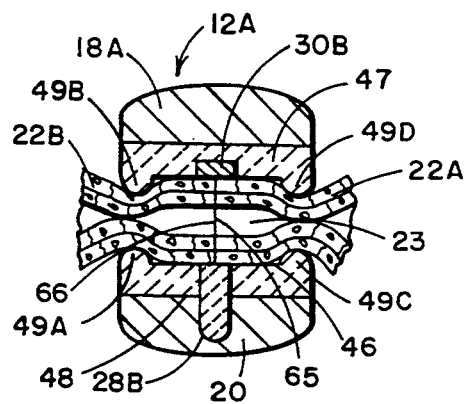
FIGS. 5A–5C are alternate bodies of the clamp shown in FIG. 3 with the fiber being located in different positions with respect to the transmissive material.
Figure 5B:
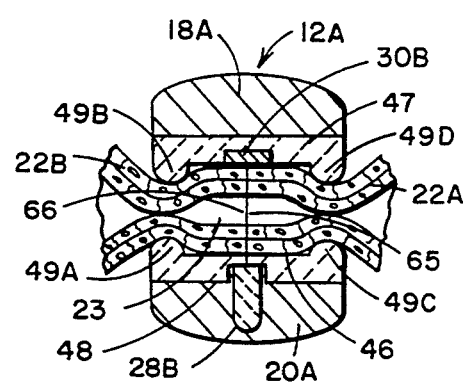
Figure 5C:
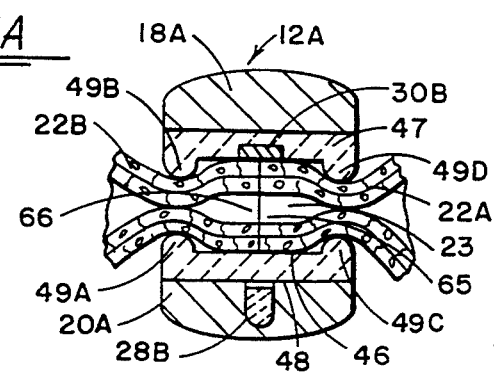

Referring to FIGS. 5A-5C, the clamp 12 has a top jaw 18a and la bottom jaw 20a. Jaws 18a and 20a have tissue engaging surfaces 46 and 47 constructed from material which is transmissive at the frequency of the energy emitted by source 16. The ends of optical media 28 may be positioned at various location in the transmissive material depending on the application and tissue type. A sensor 30b is preferably placed directly across from media 28b.

The distal end of media 28a-28d may be positioned at different locations with respect to the surface 46 or 47 of the transmissive material and vessel 22. In FIG. 5A, the distal end of media 28 extends through material surface 46 and is positioned flush with the surface 46 of jaw 20a to abut vessel 22. In FIG. 5B, the distal end of media 28 abuts one surface 48 of the transmissive material while surface 46 contacts tissue 22. In FIG. 5C, the distal end of media 28 is spaced apart from surface 48 of material while the other surface 46 of material contacts tissue 22.

Figure 6:
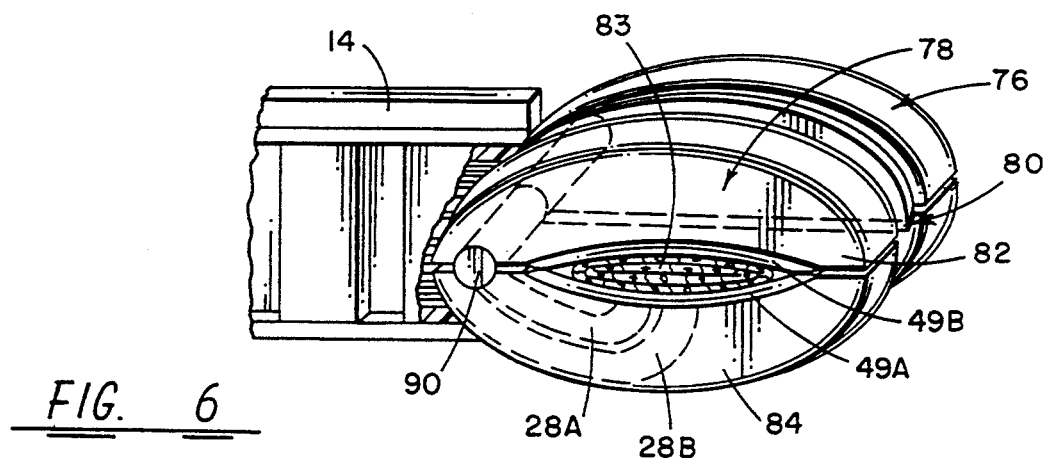
FIG. 6 is perspective view of an alternate embodiment of a clamp which can sever the tissue as well as occlude various tissue types.
Figure 7:
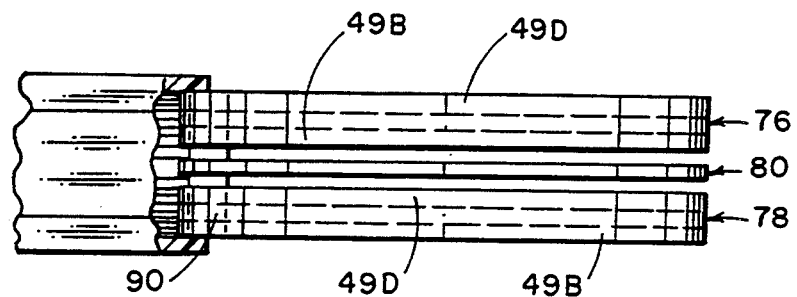
FIG. 7 is a top view of the embodiment shown in FIG. 6.

Referring to FIG. 6 and 7, there are shown clamps 76 and 78 having a knife 80 disposed there between that occludes and then transects vessel 83. Clamps 76 and 78 each have a jaw 82 and 84 respectively which pivot about pin 90 to engage vessel 83. Clamps 76 and 78 are constructed identically to clamp 12a (FIG. 2C) with jaws 82 and 84 having a radius of curvature which completely closes lumen 23 when vessel 83 is engaged. Clamps 76 and 78 also contain media 28a-28d which deliver optical energy to occlude vessel 83 in the manner previously described in connection with FIG. 2C, when the lumen 23 is closed. Knife 80 pivots about pin 90 to sever vessel 83 after being occluded. Rather than a knife, it may be preferable that a device which emits energy at a wavelength that cuts tissue be disposed between clamps 76 and 78.

This concludes the description of the preferred embodiments. A reading by those skilled in the art will bring to mind various changes without departing from the spirit and scope of the invention- It is intended, however, that the invention only be limited by the following appended claims.

What is claimed is:

1. An apparatus for causing the formation of a proteinaceous framework from denatured protein in the vicinity of biological tissue to be reconstructed, the apparatus comprising:
    an energy source for providing energy which is capable of heating the tissue to form an adhesive denatured proteinaceous substance;
    a clamp having a first jaw having a concave surface for engaging with the tissue, sad surface being formed of a layer of transmissive material which is substantially transparent to the energy being emitted by the source, said surface of the transmissive material being selected to have a thickness for maintaining a predetermined spacing between said delivering means and the tissue;
    means for delivering said energy from the source through said transmissive material to an area on the biological tissue to be reconstructed when said jaw engages the tissue, said delivery means including a plurality of optical fibers each having one end placed adjacent to the transmissive material, said plurality of fibers being positioned in said first and second jaws to direct energy at a plurality of areas that circumscribe said tissue when said tissue is engaged by said jaws; and
    means for controlling substantially all of the energy directed at the area to be within a nondestructive range bonded by a minimum rate at which tissue forms a denatured proteinaceous substance and a maximum rate at which water in the tissue would boil so that anatomical continuity of the tissue is restored after energy is delivered to the tissue.

2. An apparatus for occluding any organ having a lumen by causing the formation of a proteinaceous framework from denatured protein within the walls of the lumen being occluded, the apparatus comprising:
    a clamp having a plurality of apertures and having a surface of concave curvature shaped to compress the organ and to tightly close off the lumen when the surface of the clamp engages with the organ;
    an optical energy source for providing energy which is capable of heating tissue to form an adhesive proteinaceous substance; and
    means for sealing and thereby occluding the lumen by directing energy from the source through the compressed organ engaged with the scamp to heat the organ to a nondestructive range bounded by a minimum temperature at which tissue forms a denatured proteinaceous substance and a maximum temperature at which water in the tissue would boil, said sealing means including means for delivering the optical energy through the plurality of apertures int he clamp and through said tissue being occluded.

3. A method for reconstructing tissue by causing the formation of a proteinaceous framework from denatured protein in the vicinity of biological tissue, the method comprising the steps of:
    providing an energy source which is capable of heating the tissue to form an adhesive proteinaceous substance;
    providing a layer of material which is transmissive to the provided energy;
    engaging the tissue to be welded with the transmissive material;
    delivering the energy from the source through the engaged transmissive material to a area on the biological tissue to be reconstructed;
    controlling the energy directed at the area to be within a nondestructive range bounded by a minimum rate at which tissue forms a denatured proteinaceous substance and a maximum rate at which water in the tissue would boil;
    delivering the energy from the source by feeding the energy into on end of an optical fiber media ad directing the energy exiting the other end of the media through the material and at the area;
    placing the other end of the media adjacent the material; and
    selecting the thickness of the transmissive material to ensure that the distance between one end of the fiber optic cable and the tissue to be reconstructed is maintained at a predetermined distance.

4. A method for anastomosing biological tissue, by causing the formation of a proteinaceous framework from denatured protein on adjacent edges of the tissue being joined, the method comprising the steps of:
    providing a clamp having a first jaw that rotates about a pivot towards a second jaw;
    placing adjacent edges of a the tissue in close proximity to each other in between the jaws;

actuating the clamp to pivot the first jaw toward the second jaw to engage the tissue with sufficient pressure to force the edges of the tissue to contact;

providing energy which is capable of heating tissue to form an adhesive proteinaceous substance;

directing the energy at the edges of the tissue to heat the contacting edges of the tissue to a temperature within a nondestructive range bounded by a minimum temperature at which tissue forms a denatured proteinaceous substance and a maximum temperature at which water in the tissue would boil;

forming the tissue engaging surface of the jaws in a concave or circular shape;

extending a protrusion along an edge of the tissue engaging surface to form a ledge which forces the edges of the tissue to contact when the surface of the jaw engages the tissue;

contacting the tissue with the ledge when the jaws are activated; and directing the energy at the tissue approximation while the edges of the tissue are in contact.

* * * * *